(12) United States Patent
Yoshimine et al.

(10) Patent No.: US 8,236,018 B2
(45) Date of Patent: Aug. 7, 2012

(54) ULTRASONIC THERAPEUTIC DEVICES

(75) Inventors: Hideto Yoshimine, Hachioji (JP);
Manabu Ishikawa, Hachioji (JP);
Kenichi Kimura, Hachioji (JP);
Susumu Komagata, Ebina (JP)

(73) Assignee: Olympus Medical Systems Corp. (JP)

( * ) Notice: Subject to any disclaimer, the term of this patent is extended or adjusted under 35 U.S.C. 154(b) by 477 days.

(21) Appl. No.: 12/418,667

(22) Filed: Apr. 6, 2009

(65) Prior Publication Data

US 2009/0318945 A1     Dec. 24, 2009

Related U.S. Application Data

(60) Provisional application No. 61/073,899, filed on Jun. 19, 2008.

(51) Int. Cl.
*A61B 17/32* (2006.01)
(52) U.S. Cl. ........................................................ 606/169
(58) Field of Classification Search ................... 604/22; 606/1, 113, 169, 174
See application file for complete search history.

(56) References Cited

U.S. PATENT DOCUMENTS

| | | | |
|---|---|---|---|
| 5,906,628 A | 5/1999 | Miyawaki et al. | |
| 6,117,152 A | 9/2000 | Huitema | |
| 6,231,578 B1 | 5/2001 | Rajhansa | |
| 6,340,352 B1 | 1/2002 | Okada et al. | |
| 6,497,715 B2 | 12/2002 | Satou | 606/169 |
| 2003/0045887 A1 | 3/2003 | Sakurai et al. | |
| 2003/0204199 A1* | 10/2003 | Novak et al. | 606/169 |
| 2003/0212422 A1* | 11/2003 | Fenton et al. | 606/169 |
| 2007/0198005 A1 | 8/2007 | Ichihashi et al. | |

FOREIGN PATENT DOCUMENTS

WO    WO 98/14126    4/1998

OTHER PUBLICATIONS

Extended European Search Report dated Nov. 27, 2009 in corresponding European Patent Application No. EP 09 00 5173 (English language).
Letter from German associate dated Dec. 2, 2009 forwarding the Extended European Search Report dated Nov. 27, 2009 to Japanese associate including discussion of relevancy thereof. German associate's letter dated Dec. 2, 2009 was date stamped received by Japanese associate on Dec. 8, 2009 (English language).

* cited by examiner

*Primary Examiner* — Ryan Severson
(74) *Attorney, Agent, or Firm* — Ostrolenk Faber LLP

(57) ABSTRACT

An ultrasonic surgical instrument comprises an ultrasonic transducer producing ultrasonic vibration, a transmission member transmitted ultrasonic vibration from the proximal end to the distal end, a sheath in which the transmission member is inserted, a procedural unit provided to the distal end of the transmission member so that it projects from the distal end of the sheath, and treating a surgical target portion using ultrasonic vibration, a procedural unit main body provided in the procedural unit, a procedural member provided in the sheath so that it projects from the distal end of the sheath to treat the surgical target portion, and a procedural member main body provided at the distal end of the procedural member. In the ultrasonic surgical instrument, the procedural member main body overlaps with the procedural unit main body, and thereby, the procedural member main body and the procedural unit main body treat the portion.

6 Claims, 7 Drawing Sheets

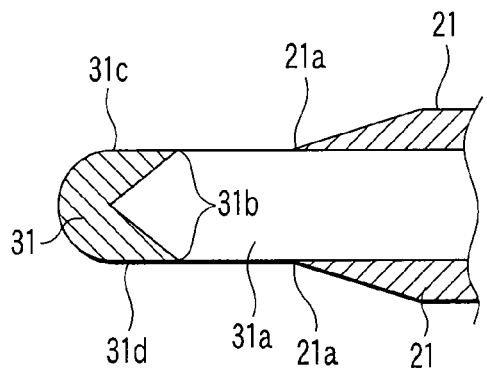
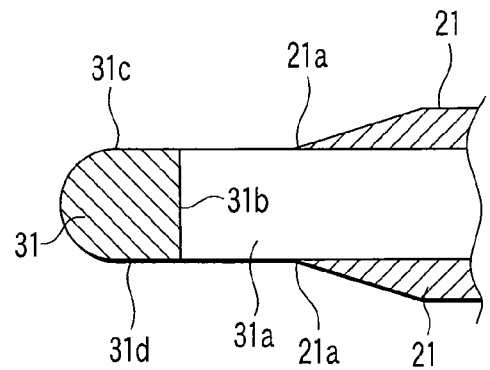
F I G. 6A   F I G. 6B
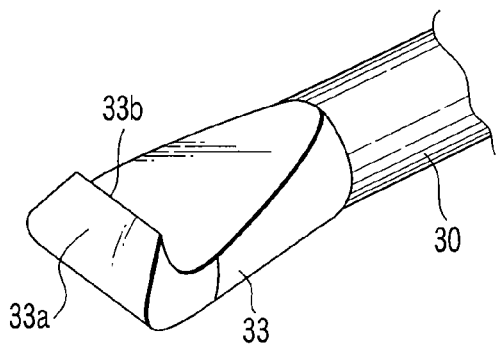
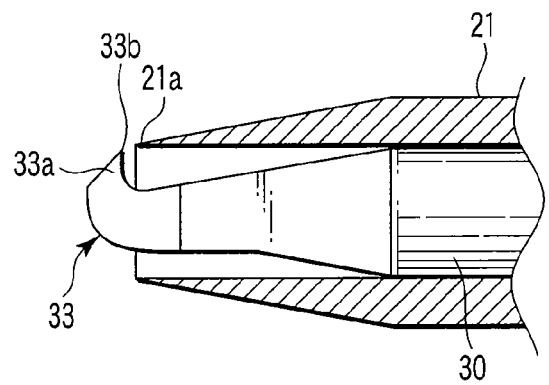
F I G. 7A   F I G. 7B
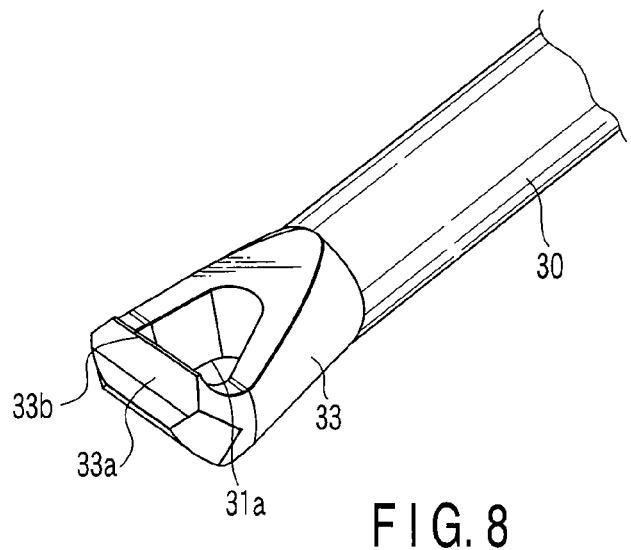
F I G. 8

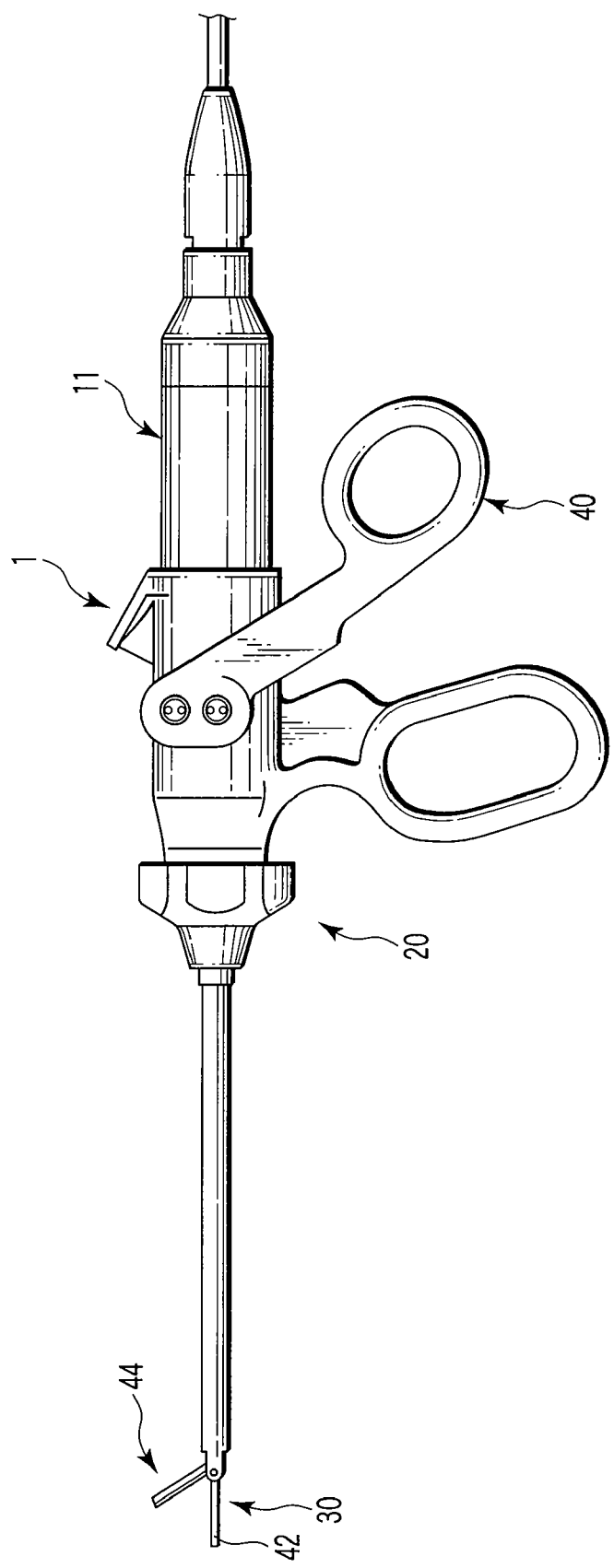
F I G. 9

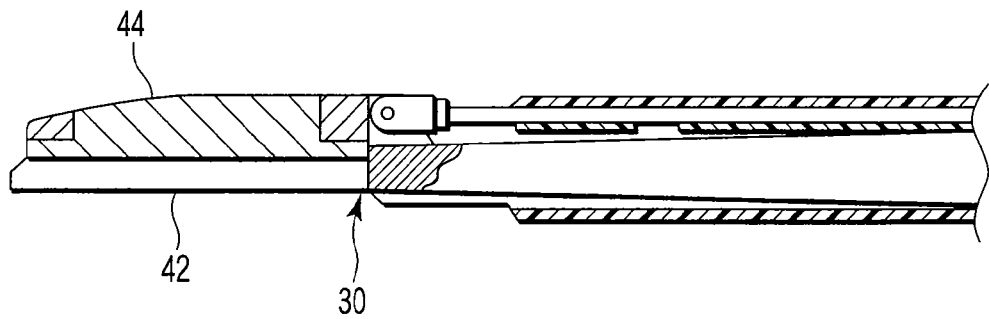
F I G. 10
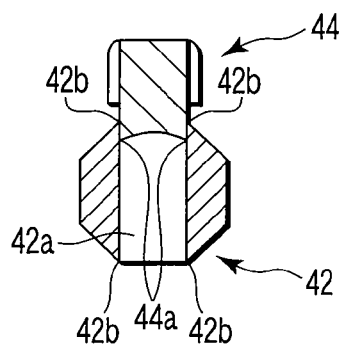
F I G. 11
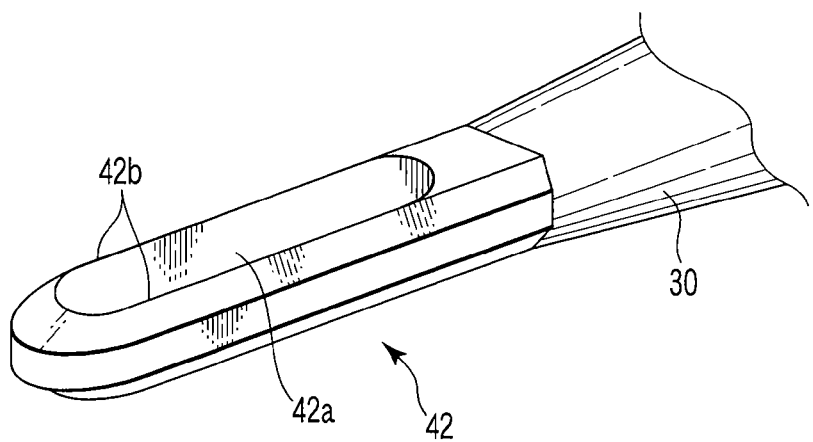
F I G. 12

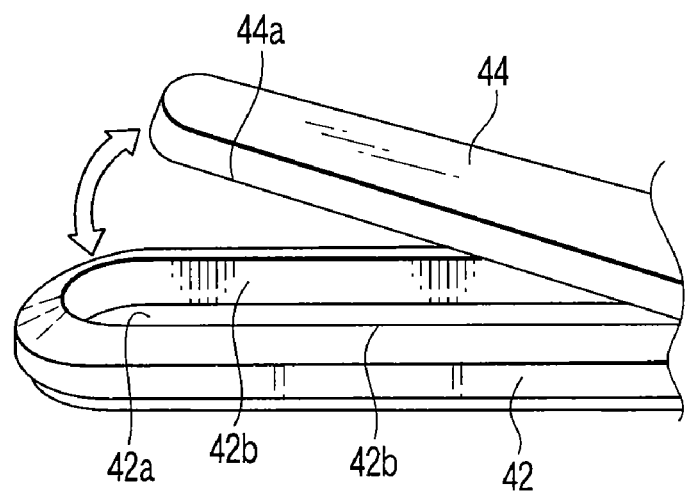
F I G. 13
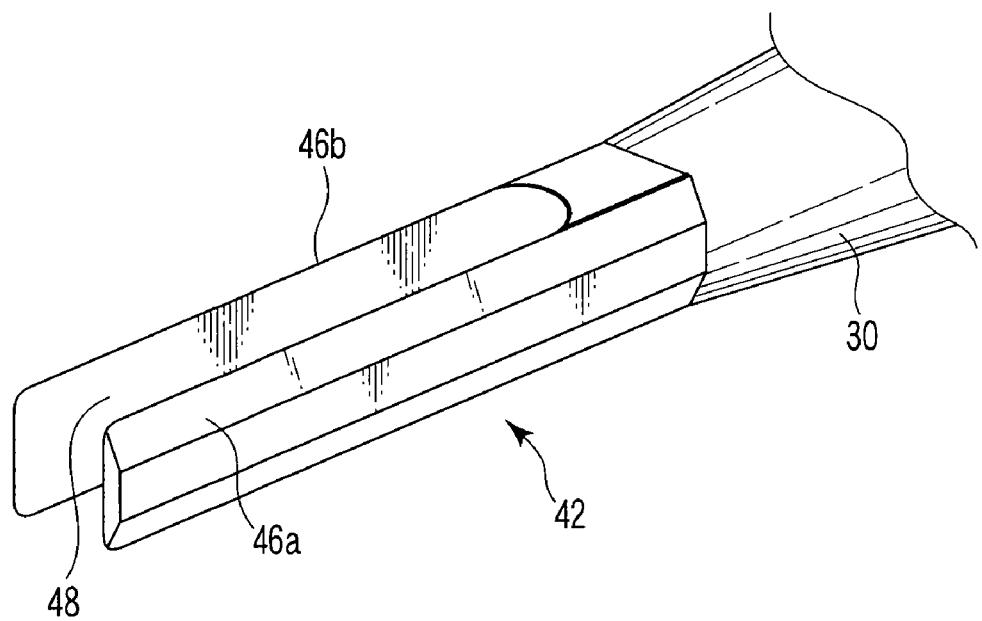
F I G. 14

ULTRASONIC THERAPEUTIC DEVICES

CROSS-REFERENCE TO RELATED APPLICATIONS

This application claims the benefit of U.S. Provisional Application No. 61/073,899, filed Jun. 19, 2008.

BACKGROUND OF THE INVENTION

1. Field of the Invention

The present invention relates to an ultrasonic surgical instrument used for orthopedics for treating bones.

2. Description of the Related Art

In general, instruments are used when hard tissues such as bones and cartilage are cut off or cut in an orthopedic operation. For example, the foregoing instruments are a cold knife, manual punch forceps, a shaver driven by an electric motor and a drill.

For example, U.S. Pat. No. 6,497,715 discloses an ultrasonic hand piece and an ultrasonic horn used therefore. The ultrasonic horn is one of members forming the ultrasonic hand piece. The ultrasonic horn has a work unit comprising at least one plane or more and an edge unit. The edge unit removes fine crushed bone tissues by the work unit. The foregoing ultrasonic hand piece and ultrasonic horn are used, and the following advantage is obtained. Specifically, in the ultrasonic hand piece used for cutting hard tissues, it is possible to prevent various disadvantages resulting from excessive cut of a knife unit to a cut portion. Further, it is possible to accurately control the knife unit in wide view so that hard tissues such as bones are precisely cut according to the surgical purpose.

BRIEF SUMMARY OF THE INVENTION

In order to solve the foregoing circumstance, an object of the present invention is to provide an ultrasonic surgical instrument, which can be easily and delicately treated the surgical target portion and perform a procedure without involving soft tissues and giving unexpected damage.

According to one aspect of the present invention, there is provided an ultrasonic surgical instrument comprising:

an ultrasonic transducer producing ultrasonic vibration;

a transmission member connected to the ultrasonic transducer at a proximal end, and transmitting ultrasonic vibration produced by the ultrasonic transducer from the proximal end to the distal end;

a sheath in which the transmission member is inserted;

a procedural unit provided to the distal end of the transmission member so that it projects from the distal end of the sheath, and treating a surgical target portion using ultrasonic vibration transmitted from the transmission member;

a procedural unit main body provided in the procedural unit, and treating the surgical target portion;

a procedural member provided in the sheath so that it projects from the distal end of the sheath to treat the surgical target portion; and a procedural member main body provided at the distal end of the procedural member to treat the surgical target portion, the procedural member main body overlapping with the procedural unit main body, and thereby, the procedural member main body and the procedural unit main body treating the surgical target portion.

Advantages of the invention will be set forth in the description which follows, and in part will be obvious from the description, or may be learned by practice of the invention.

Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 6A is a view showing a procedural unit according to a modification example;

FIG. 6B is a view showing a procedural unit according to another modification example;

FIG. 7A is a perspective view showing a procedural unit according to a second embodiment of the present invention;

FIG. 7B is a perspective view showing the distal end of a shearing member and a procedural unit;

FIG. 8 is a view showing a procedural unit according to another modification example;

FIG. 9 is a schematic view showing an ultrasonic surgical instrument used for orthopedics according to a third embodiment of the present invention;

FIG. 10 is a traverse cross-sectional view showing a procedural unit and a cutting member;

FIG. 11 is a longitudinally cross-sectional view showing a procedural unit and a cutting member;

FIG. 12 is a perspective view showing a procedural unit;

FIG. 13 is a perspective view showing a state that a procedural unit and a cutting member is rotated with respect to the procedural unit; and FIG. 14 is a view showing a procedural unit according to a modification example.

DETAILED DESCRIPTION OF THE INVENTION

Various embodiments of the present invention will be hereinafter described with reference to the accompanying drawings.

A first embodiment will be described below with reference to FIGS. 1 to 5.

Figure 1:
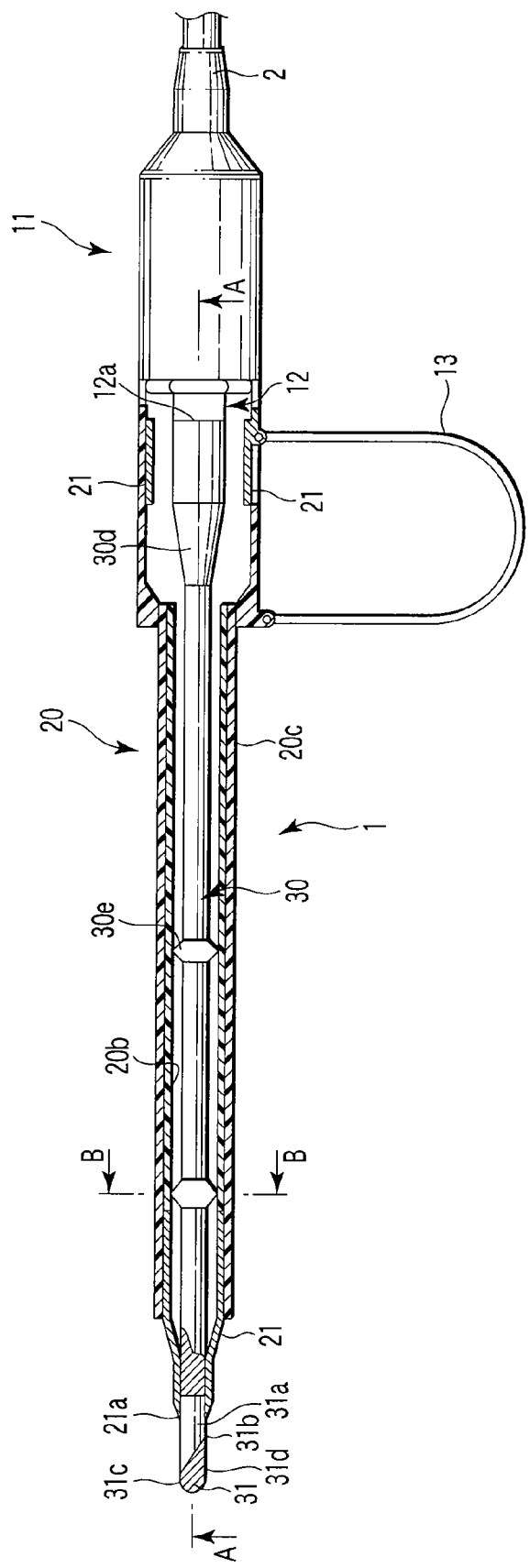
FIG. 1 is a schematic view showing an ultrasonic surgical instrument used for orthopedics according to a first embodiment of the present invention.

As shown in FIG. 1, an ultrasonic surgical instrument 1 used for orthopedics treats a surgical target portion in an orthopedic operation, for example. The surgical target portion is, for example, hard tissues such as bones and cartilage. The procedure means cut-off and cutting, for example.

The ultrasonic surgical instrument 1 has a cylindrical case 11 and a sheath 20. Specifically, the cylindrical case 11 is attached to a proximal side of the ultrasonic surgical instrument 1. The sheath 20 is attached to the distal side of the case 11.

The proximal side of the case 11 is connected with an output connection cable 2. The case 11 is connected with a power supply unit (not shown) via the output connection cable 2.

Figure 2:
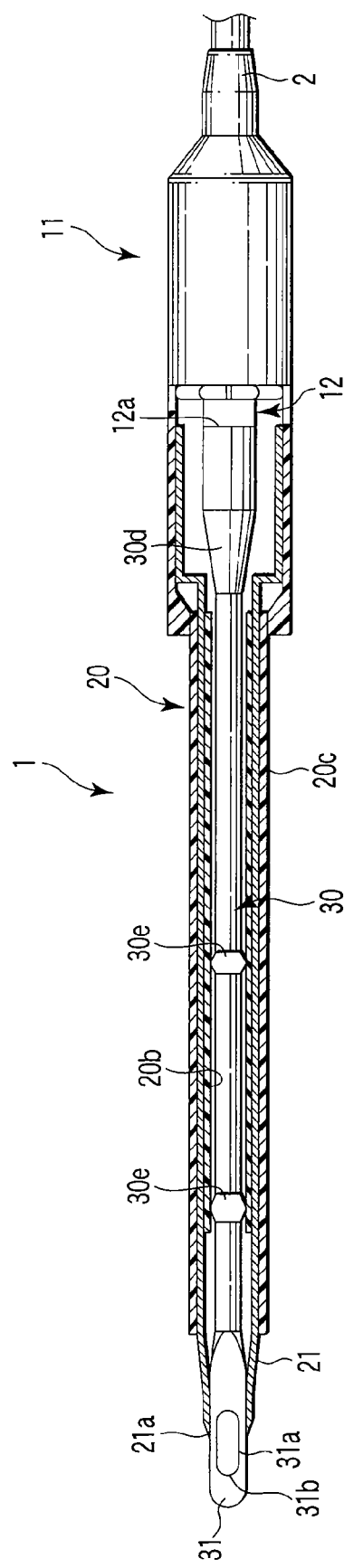
FIG. 2 is a cross-sectional view showing the ultrasonic surgical instrument taken along line A-A shown in FIG. 1.

As illustrated in FIGS. 1 and 2, an ultrasonic transducer 12 is fixedly provided in the case 11. The ultrasonic transducer 12 has a piezoelectric element and a horn 12a. Specifically, the piezoelectric element produces ultrasonic vibration. The horn 12a is attached to the distal end of the ultrasonic transducer 12 in the longitudinal direction of the case 11, and amplifies ultrasonic vibration.

The ultrasonic transducer 12 is a member, which converts electrical energy to ultrasonic vibration. The energy is produced by the power supply unit (not shown), and then, supplied to the ultrasonic transducer 12 from the driver via the output connection cable 2, and thus, converted to ultrasonic vibration.

For example, the ultrasonic transducer 12 is a bolt-clamped langevin type transducer (BLT).

The horn 12a is made of metallic materials such as titanium, duralumin and stainless.

The distal end of the horn 12a is attached with a probe 30, which is inserted in the sheath 20. The probe 30 is a transmission member for transmitting ultrasonic vibration amplified by the horn 12a to the distal side of the ultrasonic surgical instrument 1. The probe 30 is removably fastened (fixed) to the horn 12a using a screw, for example. In other words, the probe 30 is connected to the ultrasonic transducer 12 via the horn 12a at the proximal end of the probe 30. Therefore, the probe 30 transmits ultrasonic vibration produced by the ultrasonic transducer 12 from the proximal end of the probe 30 to the distal end (distal end of the ultrasonic surgical instrument 1) thereof.

The probe 30 is made of metallic materials such as titanium, duralumin and stainless.

The probe 30 further has a horn 30d on the proximal side of the probe 30. The horn 30d further amplifies ultrasonic vibration transmitted from the ultrasonic transducer 12 (horn 12a).

The distal end of the probe 30 is provided with a procedural unit 31, which projects from the distal end of the sheath 20. The procedural unit 31 treats a surgical target portion using ultrasonic vibration produced by the ultrasonic transducer 12 and transmitted from the probe 30. The procedural unit 31 has a flat shape approximately. The procedural unit 31 contacts with the surgical target portion, and thereby, treats it using ultrasonic vibration.

The probe 30 further has a support member (rubber lining) 30e at an intermediate (antinode) position of the ultrasonic vibration. The support member 30e is used for fixing the probe 30 in the sheath 20. For example, the support member 30e is made of a resin such as silicon rubber.

The procedural unit 31 has a long-diameter loop shape in the longitudinal direction of the case 11 (in the longitudinal direction of the probe 30). The procedural unit 31 is formed with an opening 31a, which penetrates in the thickness direction of the procedural unit 31. The distal end of the opening 31a in the longitudinal direction of the probe 30 is formed with a shearing edge 31b (see FIG. 4). The shearing edge 31b is sheared a surgical target portion together with an outer blade 21a described later. The shearing edge 31b is formed in a desired inclined state to shear a surgical target portion. The shearing edge 31b is formed in a desired inclined state to the longitudinal direction of the probe 30 at the distal end of the longitudinal direction of the probe 30 in the loop. In other words, the shearing edge 31b is formed in a desired state of being inclined from one surface (e.g., upper surface 31c) of the procedural unit 31 to the other surface (e.g., lower surface 31d). The shearing edge 31b is a procedural unit main body for shearing a surgical target portion together with an outer blade 21a described later, that is, a shearing portion.

The sheath 20 is provided with a grip 13 for grasping the ultrasonic surgical instrument 1. The grip 13 has an elastic force. The grip 13 is a control unit, which slides a shearing member 21 to the probe 30 including the procedural unit 31 along the longitudinal direction of the probe 30.

As described above, the case 11 is provided with the sheath 20 in which the probe 30 is inserted, at the distal end of the case 11. In other words, the sheath 20 covers the probe 30.

Figure 3:
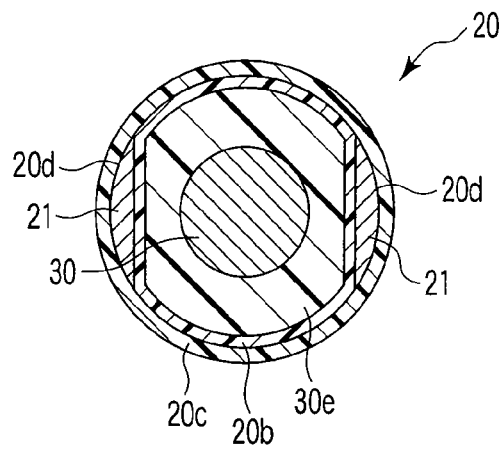
FIG. 3 is a cross-sectional view showing the ultrasonic surgical instrument taken along line B-B shown in FIG. 1.

As seen from FIGS. 1 to 3, the sheath 20 has an inner tube 20b covering the support member 30e, and an outer tube 20c covering the inner tube 20b.

The foregoing inner and outer tubes 20b and 20c are made of a metallic material such as stainless, for example.

As shown in FIG. 3, the outer tube 20c has a cylindrical shape while the inner tube 20b has a non-cylindrical shape. Thus, a space 20d is formed between the outer and inner tubes 20c and 20b. The space 20d is formed along the longitudinal direction of the sheath 20. The space 20d is provided with a shearing member 21. The proximal end of the shearing member 21 is connected to the grip 13 as shown in FIG. 1. Moreover, the distal end of the shearing member 21 projects from the distal end of the sheath 20 like the procedural unit 31 as shown in FIGS. 1 and 2, and has an outer metallic blade 21a. Namely, the shearing member 21 is provided in the sheath 20 so that it projects from the distal end of the sheath 20, and a shearing member for shearing a surgical target portion. In other words, the shearing member 21 is a procedural member for shearing the surgical target portion. The outer blade 21a is a procedural member main body for shearing the surgical target portion together with the shearing edge 31b.

The shearing member 21 is slidable along the longitudinal direction of the probe 30 with respect to the probe 30 including procedural unit 31 by operating the grip 13. The foregoing operation of the grip 13 means that a doctor (operator) grasps or releases the grip 13. Namely, the shearing member 21 has a slidable shape in the sheath 20 (between outer and inner tubes 20c and 20b, that is, in the space 20d). In this case, the shearing member 21 is slidable along the longitudinal direction of the sheath 20 with respect to the probe 30 including procedural unit 31 by operating the grip 13. Therefore, the shape of the shearing member 21 has no need of the same as that of the space 20d.

Figure 5:
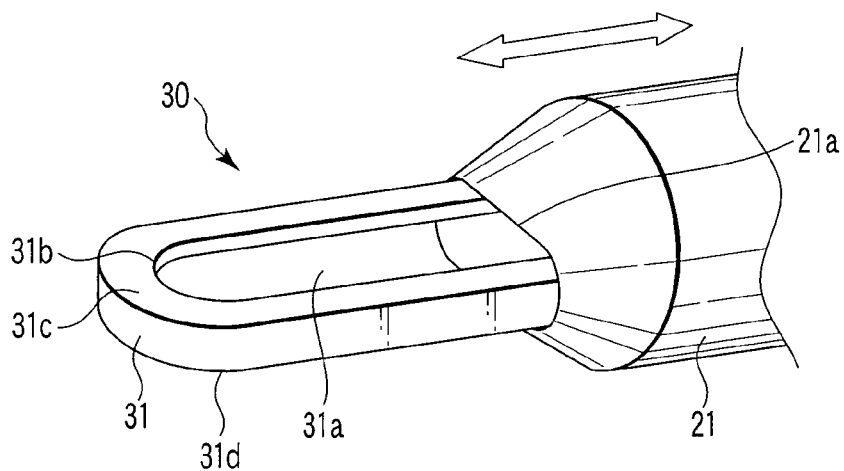
FIG. 5 is a perspective view showing the distal end of a shearing member and a procedural unit.

When the shearing member 21 slides along the longitudinal direction of the sheath 20 with respect to the probe 30 including procedural unit 31, the outer blade 21a slides on the procedural unit 31 (upper and lower surfaces 31c and 31d), as depicted in FIG. 5. In this way, the shearing member 21 moves to the shearing edge 31b. At that time, the outer blade 21a overlaps with the shearing edge 31, and thereby, the outer blade 21a and the shearing edge 31b shear a surgical target portion.

The operation according to this embodiment will be described below.

The procedural unit 31 contacts with a surgical target portion of a living tissue. In this state, electrical energy produced by the power supply unit (not shown) is supplied from the drive (not shown) to the ultrasonic transducer 12 via the output connection cable 2. Then, the foregoing energy is converted to ultrasonic vibration by the ultrasonic transducer 12. The ultrasonic vibration is amplified by the horn 12a, and transmitted to the probe 30. Then the ultrasonic vibration further is amplified by the horn 30d and then, transmitted from the probe 30 to the surgical target portion via the procedural unit 31. Namely, the ultrasonic vibration is transmitted from the proximal end of the probe 30 to the distal end thereof. In this way, the surgical target portion is treated by means of the procedural unit 31.

When a doctor (operator) grasps the grip 13, the shearing member 21 slides toward the distal end of the procedural unit 31 along the longitudinal direction of the probe 30. In this way, the outer blade 21a slides on the procedural unit 31 (upper and lower surfaces 31c and 31d), and thus, moves to the shearing edge 31b. In this case, the outer blade 21a overlaps with the shearing edge 31b, and thereby, the surgical target portion is sheared by the outer blade 21a and the ultrasonically vibrating shearing edge 31b.

Conversely, when a doctor releases the grip 13, the grip 13 is returned to the previous state that the doctor grasps the grip 13, by elastic force. In this way, the shearing member 21 slides toward the distal end of the sheath 20 along the longitudinal direction of the probe 30.

As described above, according to this embodiment, the surgical target portion is easily treated by the procedural unit 31 using ultrasonic vibration. In addition, according to this embodiment, the grip 13 is grasped so that the sharing member 21 is slidable. In this way, the surgical target portion is treated by the outer blade 21a and the ultrasonically vibrating shearing edge 31b. According to this embodiment, the surgical target portion is easily and delicately treated. Therefore, this serves to treat the surgical target portion without giving damage to soft tissues (without involving soft tissues). As a result, the surgical target portion is treated without giving unexpected damage.

According to this embodiment, the surgical target portion is placed in the opening 31a, and thereby, a procedure such as cutting is easily performed using ultrasonic vibration.

As seen from the foregoing description, this embodiment can provide two procedures, that is, cutting and shearing using ultrasonic vibration.

According to this embodiment, a sheared surface of the surgical target portion is made smooth by ultrasonic vibration of the shearing edge 31b. This serves to relieve pain of a patient after being operated.

According to this embodiment, the shearing member 21 is slid to treat a surgical target portion. Therefore, a procedure is carried out without involving soft tissues, and without giving unexpected damage (i.e., it is possible to prevent damage of the surgical target portion).

According to this embodiment, the grip 13 is grasped, and thereby, the surgical target portion is sheared. Therefore, the shearing operation is easy.

Figure 4:
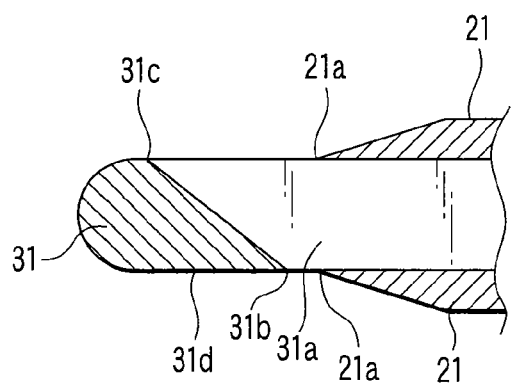
FIG. 4 is a cross-sectional view showing the distal end of a shearing member and a procedural unit.

It should be noted that the shearing edge 31b has no need to be limited to the shape shown in FIG. 4.

For example, the shearing edge 31b may be formed obliquely from the upper surface 31c of the procedural unit 31 toward the longitudinal direction of the probe 30 and from the lower surface 31d thereof toward the same, as seen from FIG. 6A.

Moreover, as shown in FIG. 6B, the shearing edge 31b may be formed vertically from the upper surface 31c of the procedural unit 31 to the lower surface 31d with respect to the longitudinal direction of the probe 30.

A second embodiment of the present invention will be described below with reference to FIGS. 7A and 7B. The same numbers are used to designate portions having the same structure as the first embodiment and its modification example, and the explanation is omitted.

A procedural unit 33 of this second embodiment has no opening 31a. The procedural unit 33 is integrally formed with a projecting portion 33, which vertically projects with respect to the longitudinal direction of a probe 30. In other words, the procedural unit 33 including the projecting portion 33a has a hook shape. The projecting portion 33a has a shearing edge 33b (procedural unit main body), which is a shearing portion same as the shearing edge 31b, at the chip end of the vertically projecting portion 33a. Further, the projecting portion 33a has a desired height so that the shearing edge 33b overlaps with an outer blade 21a in the vertical direction.

When the procedural unit 33 treats a surgical target portion, an ultrasonic surgical instrument 1 including the procedural unit 33 moves in a state that the procedural unit 33 projects from the distal end of a sheath 20. The projecting portion 33a contacts with the surgical target portion, and thereby, the procedural unit 33 treats the surgical target portion using ultrasonic vibration.

When a doctor (operator) grasps a grip 13, a shearing member 21 slides toward the projecting portion 33a along the longitudinal direction of the probe 30 as shown in FIG. 7B. In this way, an outer blade 21a moves toward the shearing edge 33b. At that time, the outer blade 21a overlaps with the shearing edge 33b, and thereby, the surgical target portion is cut or treated by the outer blade 21a and the shearing edge 33b.

According to the second embodiment, the same effect as the first embodiment is obtained.

The procedural unit 33 of this embodiment has a hook shape. Therefore, according to this embodiment, the procedural unit 33 easily hooks the surgical target portion. This serves to simplify the operation until a procedure is carried out.

The procedural unit 33 has a hook shape which has the opening 31a (a long-diameter loop shape in the longitudinal direction of the probe 30) as shown in FIG. 8.

A third embodiment of the present invention will be described below with reference to FIGS. 9 and 13. The same numbers are used to designate portions having the same structure as the first embodiment and its modification example, and the explanation is omitted.

An ultrasonic surgical instrument 1 of this third embodiment has a cutting member 44. When a control unit 40 is rotated, the cutting member 44 is rotated with respect to a procedural unit 42 in accordance with the rotation of the control unit 40. The cutting member 44 is rotatable with respect to the procedural unit 42, and is a procedural member for cutting a surgical target portion.

The procedural unit 42 has a flat shape, and contacts with a surgical target portion to treat it using ultrasonic vibration. The procedural unit 42 has a large-diameter loop shape in the longitudinal direction of a case 11 (of the probe 30). The procedural unit 42 is formed with an opening 42a, which penetrates in the thickness direction of the procedural unit 42. The opening 42a has a cutting edge 42b at the outer peripheral portion. The cutting edge 42b is a cutting unit for cutting a surgical target portion together with a blade 44a described later. In other words, the cutting edge 42b is formed along the longitudinal direction in the loop. The cutting edge 42b is a procedural unit main body for cutting a surgical target portion together with a blade 44a described later.

A cutting member 44 is inserted in the opening 42a. The cutting member 44 rotates with respect to the procedural unit 42. Further, the cutting member 44 has a metallic blade 44a, which is formed to be fitted in the opening 42a. The blade 44a is a procedural member main body.

The cutting member 44 is rotatable with respect to the probe 30 including the procedural unit 42 by operating the control unit 40. The rotation mechanism for rotating the cutting member 44 in accordance with the operation of the control unit 40 is omitted for simplification of the drawings. However, it is obvious for the skilled person to include a known rotation mechanism.

When the cutting member 44 is rotated, the blade 44a moves toward the cutting edge 42b. At that time, the blade 44a overlaps with the cutting edge 42b so that a surgical target portion is held between the blade 44a and the cutting edge 42b. In this way, the blade 44a and the cutting edge 42b cut the surgical target portion.

The operation of this third embodiment will be described below.

When a doctor (operator) grasps the control unit 40, the cutting member 44 is rotated toward the opening 42a. In this way, the blade 44a moves toward the cutting edge 42b.

In this case, living tissues, that is, a surgical target portion is held between the procedural unit 42 and the cutting member 44. The cutting member 44 further rotates toward the opening 42a from the foregoing state. Electrical energy produced by the power supply unit is converted to ultrasonic vibration as in the first embodiment. The ultrasonic vibration is amplified as in the first embodiment, and then, transmitted to the probe 30. In this case, the ultrasonic vibration is transmitted to a surgical target portion via the procedural unit 42.

Then, the blade 44a overlaps with the cutting edge 42b so that a surgical target portion is held between the blade 44a and the cutting edge 42b. In this way, the blade 44a and the cutting edge 42b cut the surgical target portion.

According to this embodiment, the same effect as the first embodiment is obtained.

According to this embodiment, the cutting member 44 is rotated toward the opening 42a so that a surgical target portion is held between the blade 44a and the cutting edge 42b. Therefore, this serves to cut the surgical target portion only. In addition, according to this embodiment, the surgical target portion is treated in a state of being held between there. Therefore, a surgical target portion having some thickness is easily cut.

The procedural unit 42 of this embodiment is not limited to the foregoing shape. For example, as seen from FIG. 14, the procedural unit 42 has a U-letter shape when being viewed from the vertical direction in the longitudinal direction of the probe 30. The procedural unit 42 has a first cutting edge 46a, which is one of the facing U-letter sides, and a second cutting edge 46b, which is the other thereof. The foregoing first and second cutting edges 46a and 46b are a procedural unit main body. Namely, the first and second cutting edges 46a and 46b are provided at one side of the U-letter shape and the other side thereof, respectively. Further, the first and second cutting edges 46a and 46b are provided in parallel along the longitudinal direction of the probe 30. The cutting member 44 rotating to the procedural unit 42 is inserted in a space 48 formed between the first and second cutting edges 46a and 46b.

The present invention is not limited to the foregoing embodiments. In the inventive stage, constituent elements may be modified and embodied without departing from the subject matter. A plurality of constituent elements disclosed in the foregoing embodiments are properly combined, and thereby, various inventions can be provided.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic surgical instrument comprising:
an ultrasonic transducer producing ultrasonic vibration;
a transmission member connected to the ultrasonic transducer at a proximal end, and configured to transmit ultrasonic vibration produced by the ultrasonic transducer from the proximal end to a distal end of the transmission member;
a sheath in which the transmission member is inserted;
a procedural unit provided to the distal end of the transmission member so that it projects from a distal end of the sheath, and is configured for treating a surgical target portion using ultrasonic vibration transmitted from the transmission member;
a procedural unit main body provided in the procedural unit, and configured for treating the surgical target portion;
a procedural member provided in the sheath so that it projects from the distal end of the sheath to treat the surgical target portion; and
a procedural member main body provided at a distal end of the procedural member to treat the surgical target portion,
the procedural member main body overlapping with the procedural unit main body, and thereby, the procedural member main body and the procedural unit main body being configured for treating the surgical target portion,
wherein the procedural unit has a large-diameter loop shape in a longitudinal direction of the transmission member, the loop shape being formed with an opening which is configured to penetrate the procedural unit in a thickness direction thereof and in which the surgical target portion is placed.

2. The instrument according to claim 1, wherein the procedural member is a shearing member, which slides along a longitudinal direction of the transmission member with respect to the transmission member, and the procedural unit main body is a shearing portion, and further, the procedural member main body and the loop shape of the procedural unit of the procedural unit main body are configured to shear the surgical target portion.

3. The instrument according to claim 2, wherein the procedural unit main body is formed at a desired inclined state relative to the longitudinal direction of the transmission member at the distal end of the longitudinal direction of the transmission member in a loop, and extends from an upper surface to a lower surface of the procedural unit.

4. The instrument according to claim 1, wherein
the sheath comprises a non-cylindrical inner tube in which the transmission member is inserted and a substantially cylindrical outer tube which covers the inner tube, and
the procedural member is provided between the inner tube and the outer tube in a radial direction of the sheath, extends along a longitudinal direction of the sheath, and slides along the longitudinal direction of the transmission member with respect to an outer surface of the inner tube and an inner surface of the outer tube.

5. The instrument according to claim 1, further comprising an elastic member having an elastic force to allow the procedural member to slide toward the distal end of the sheath along the longitudinal direction of the transmission member.

6. The instrument according to claim 1, wherein the procedural unit main body is formed obliquely with respect to a longitudinal axis of the transmission member, from an upper surface and a lower surface of the procedural unit toward the longitudinal axis of the transmission member and a distal end of the procedural unit.

* * * * *